US007563875B2

(12) United States Patent
Palys et al.

(10) Patent No.: US 7,563,875 B2
(45) Date of Patent: Jul. 21, 2009

(54) RECOMBINANT CHIMERIC HUMAN ANTI-BOTULINUM ANTIBODIES

(75) Inventors: Thomas J. Palys, Cascade, MD (US); Randal J. Schoepp, Frederick, MD (US); Kara E. Schmid, Frederick, MD (US)

(73) Assignee: The United States of America as represented by the Sercretary of the Army, Washington, DC (US)

( * ) Notice: Subject to any disclaimer, the term of this patent is extended or adjusted under 35 U.S.C. 154(b) by 70 days.

(21) Appl. No.: 11/384,712

(22) Filed: Mar. 20, 2006

(65) Prior Publication Data

US 2007/0218516 A1 Sep. 20, 2007

(51) Int. Cl.
*C12P 21/08* (2006.01)
*G01N 33/577* (2006.01)

(52) U.S. Cl. .................................. 530/388.4; 435/7.4

(58) Field of Classification Search ....................... None
See application file for complete search history.

(56) References Cited

U.S. PATENT DOCUMENTS 5,932,449 A * 8/1999 Emanuel et al. ............ 435/70.1

OTHER PUBLICATIONS

Morrison et al. (PNAS, 81:6851-6855, 1984).*

* cited by examiner

*Primary Examiner*—Mark Navarro
*Assistant Examiner*—Brian J Gangle
(74) *Attorney, Agent, or Firm*—Elizabeth Arwine

(57) ABSTRACT

In this application is described the production of recombinant, chimeric, humanized antibodies specific for both BoNt/A and BoNT/B. The humanized antibodies were converted from a mouse anti-BoNT/A/B Fab fragment into a whole human IgG1 antibody. The antibodies are useful in assays for detecting human exposure to BoNT/A and BoNT/B.

13 Claims, 7 Drawing Sheets

FIG. 1

Mouse anti-botulinum BotFab5 $V_H$

Mouse anti-botulinum BotFab5 $V_L$

Human Kappa Light Chain

Human IgG1 Fc

Human IgG1 Heavy Chain

RECOMBINANT CHIMERIC HUMAN ANTI-BOTULINUM ANTIBODIES

INTRODUCTION

Infection of humans by many microorganisms leads to the initiation of a humoral immune response that can be used in the diagnosis of the disease. Specific IgM or IgG responses to a particular infectious agent can be measured by antibody based diagnostic tests such as ELISA, electrochemiluminescence, immunochromatography, particle agglutination ELISA, biosensor or other similar assays.

These assays require the use of reactive human sera as a positive control. The positive control reagent is usually serum taken from a patient or animal known to have a positive reaction to the antigen being tested. It is becoming increasingly difficult to source sufficient quantities of immune human sera or plasma, particularly as diagnostic tests for rarer diseases become available. For botulinum neurotoxin toxicity, broadly cross-reactive antibodies specific to more than one of the botulinum neurotoxins (BoNT) serotypes A, B, C, D, E, F and G are needed to develop immunoassays that can detect a wide range of BoNT simultaneously or that can be used in the serological assays of human exposure to several BoNT at once. Whole murine antibodies or any type of antibody fragment, such as Fab fragment or single chain Fv (scFv) fragment, although available, can not be used as a positive control for BoNT in serological tests for human exposure to BoNT. Only a positive human control antibody for BoNT can be used to validate serological tests for human exposure to BoNT. Whole human antibodies to BoNT, however, are very difficult to obtain since they can only be derived from the serum of individuals exposed or immune to BoNT.

Therefore, there is a need for a source of positive control reagents, such as human antibodies to BoNT, which does not rely on human donors.

SUMMARY OF THE INVENTION

The present invention satisfies the need discussed above. The present invention describes whole chimeric human antibodies, rHuBF5-A6 and rHuBF5-B1. The antibodies of the present invention were converted from a mouse anti-BoNT serotype/A serotype/B Fab fragment, BotFab5, into a whole human IgG$_1$ antibody. Variable heavy ($V_H$) and light ($V_L$) genes of the mouse anti-botulinum Fab phagemid were cloned into specialized human IgG$_1$ expression vectors to generate heavy-chain IgG vector and light chain expression vector. The linearized vectors were transfected into a myeloma cell line and the cell line selected for expression of the whole human IgG$_1$ antibody specific for botulinum toxin.

The whole antibodies of the present invention present several advantages over other reagents used in detecting BoNT directly or for conducting serological tests for exposure to BoNT. First, the whole chimeric antibodies of the present invention possess greater compatibility with commonly used immunoassay platforms such as ELISA and electrochemiluminescence (ECL) than single chain antibody fragments (scFv) or Fabs since most immunoassays are based on whole antibody reagents (e.g. primary antibodies, secondary antibodies, whole antibody conjugates). Second, it is well known that whole antibodies are more stable than scFv and Fab antibody fragments. Third, rHuBF5-A6 and rHuBF5-B1 are specific for both BoNT/A and BoNT/B, whereas most other anti-BoNT antibodies and antibody fragments are either specific for BoNT/A or BoNT/B, but not both. Fourth, rHuBF5-A6 and rHuBF5-B1 are produced and secreted by myelomas in cell supernatant and are readily purified from supernatant and can therefore be purified more easily and in greater quantity than antibody fragments. Fifth, rHuBF5-A6 and rHuBF5-B1 contain a human IgG$_1$ Fc region. This enables the antibodies to be used as a positive control reagent to validate serological tests for individual exposure to BoNT/A or BoNT/B. Mouse-derived antibodies and mouse or human antibody fragments can not be used as a positive control reagent in a human serological test. Either rHuBF5-A6 or rHuBF5-B1 can therefore serve as a readily producible human positive control reagent for seroanalysis of BoNT exposure, thus obviating the need for obtaining scarce anti-botulinum human serum for assay validation.

Therefore, it is an object of the present invention to provide human IgG$_1$ monoclonal antibodies which are specific for both BoNT/A and BoNT/B. Such antibodies are, for instance rHuBF5-A6, produced by the cell line Y1-BF5-A6, deposited under the Budapest Treaty at American Type Culture Collection (ATCC), Manassas, Va. on Jun. 28, 2006 having ATCC accession no. PTA-7673 and antibody rHuBF5-B1, produced by the cell line Y1-BF5-B1, deposited under the Budapest Treaty at ATCC on Jun. 28, 2006, having ATCC accession no. PTA-7674.

It is another object of the invention to provide antibodies that are functionally equivalent to the antibodies listed above. These functionally equivalent antibodies substantially share at least one major functional property with an antibody listed above and herein described comprising: binding specificity to both BoNT/A and BoNT/B, or competition for the same binding sites on BoNT/A and BoNT/B. The antibodies can be of any species and of any class such as IgG, IgM, or IgA or any subclass such as IgG1, IgG2a, and other subclasses known in the art. Further, the antibodies can be produced in any organism or cell line, including bacteria, plant, insect, mammal or other type of cell or cell line which produces antibodies with desired characteristics.

It is yet another object of the present invention to provide a chimeric antibody comprising an antigen binding region derived from a first species antibody, such as human, murine or other rodent, simian or non-human primate, shark or other fish, bovine, equine, porcine, ovine, camelid, rabbits or other leporids, and avian sources, and a constant region which comprises at least one human constant region or epitope thereof from a second species wherein the first species is different than the second species.

The invention further provides: isolated nucleic acids encoding (1) the heavy chain variable domains and (2) the light chain variable domains of the antibody or polypeptide chain; vectors comprising nucleic acids encoding the antibody or polypeptide chains, optionally, operably linked to control sequences recognized by a host cell transformed with the vector; nuclei acids (1) and (2) may be present in the same, or different, vector; host cell comprising (e.g. transformed with) nucleic acid(s) encoding the antibody or polypeptide chains; a method for producing the antibody or polypeptide chain comprising culturing the host cell so that the nucleic acid is expressed and, optionally, recovering the antibody or polypeptide chain from the host cell culture (e.g. from the host cell culture medium). Nucleic acids for the heavy chain variable domain and the light chain variable domain are preferably co-expressed by a host cell transformed with both (1) and (2).

It is yet another object of the present invention to provide for a composition comprising the chimeric, humanized antibodies according to the present invention, as well as to methods of using the composition for the prevention and/or therapeutic treatment of botulinum intoxication in vivo, and/or for improved detection of botulinum intoxication in vitro or in vivo.

It is still another object of the present invention to provide chimeric, humanized antibodies for use as a positive control in serological tests for the detection of BoNT/A and/or BoNT/B. The antibodies of the invention provide advantages in that they are bispecific and can detect both BoNT/A and BoNT/B. They are humanized antibodies and can therefore be used instead of scarce anti-botulinum human sera in assays detecting human exposure to BoNT/A and/or BoNT/B. They are intact, whole antibodies which are stable, can be easily isolated in large quantities, and are easy to adapt to existing immunoassays.

It is still another object of the present invention to provide novel immunoprobes and test kits for detection of BoNT/A and BoNT/B. For immunoprobes, the antibodies are directly or indirectly attached to a suitable reporter molecule, e.g., ruthenium or fluorescein, an enzyme or a radionuclide. The test kit includes a container holding one or more antibodies according to the present invention and instructions for using the antibodies for the purpose of binding to BoNT/A and BoNT/B to form an immunological complex and detecting the formation of the immunological complex such that presence or absence of the immunological complex correlates with presence or absence of said BoNT/A or BoNT/B.

BRIEF DESCRIPTION OF THE DRAWINGS

These and other features, aspects, and advantages of the present invention will become better understood with reference to the following description and appended claims, and accompanying drawings where:

FIG. 1. Diagram of rHu-BF5 chimeric recombinant antibody.

FIG. 8. Titration binding curves of rHu-BF5-A6 and rHu-BF5-B1. Titration in capture ELISA showed that 5.0 ug/ml of both rHu-BF5-A6 and rHu-BF5-B1 detected as low as 0.3 ng of botulinum toxin A and 0.4 ng of botulinum toxin B. When used at as low as 0.31 ug/ml, rHu-BF5-A6 detected down to 4.7 ng of botulinum toxin A and 5.9 ng of botulinum toxin B.

FIG. 10. Comparison of recombinant human IgG antibodies to mouse BotFab5. The recombinant antibodies and the BotFab5 were compared for detection of botulinum toxoid by capture ELISA.

Figure 2:
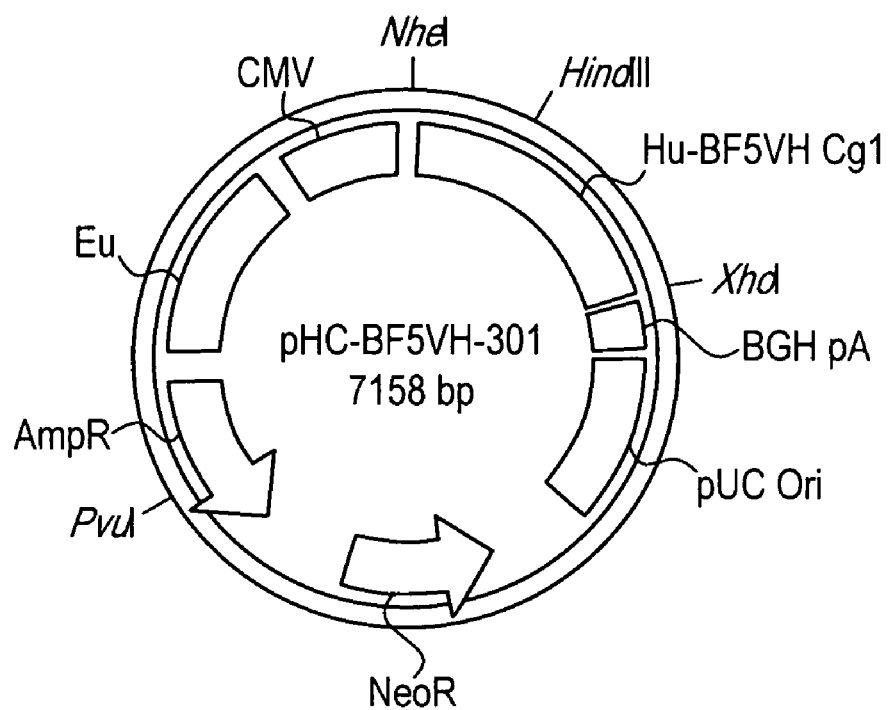
FIG. 2. Heavy chain expression vector, pHC-BF5VH-301. Hu-BF5VH Cg1, chimeric human-BotFab5$V_H$ gamma 1 gene; BGH pA, Bovine Growth Hormone poly A sequence; pUC19 Ori, pUC19 origin sequence; Neo$^R$, neomycin (geneticin) resistance gene; AmpR, ampicillin resistance gene; Eu, murine enhancer sequence; CMV, cytomegalovirus promoter sequence.
Figure 3:
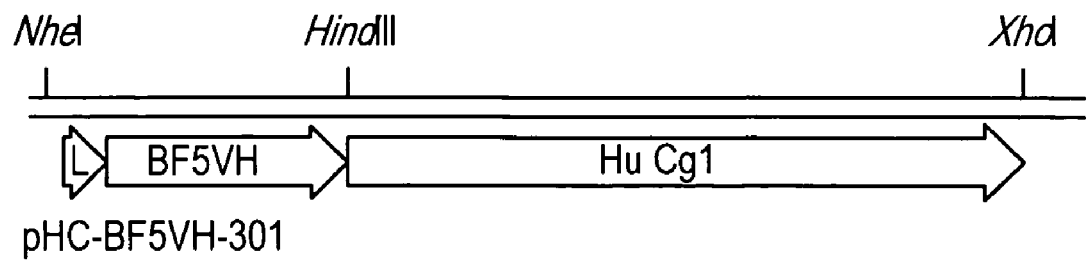
FIG. 3. Cloning site heavy chain expression vector, pHC-BF5VH-301. L, leader sequence; BF5VH, BothFab5 variable heavy chain gene (SEQ ID NO:1); Hu Cg1, human gamma 1 constant gene.

Plates were coated with 2 ug/ml of either A6, B1 or BotFab5. Plates were incubated with indicated amount of botulinum toxoid and detected with horse anti-botulinum sera and goat anti-horse HRP conjugate. Data are presented as OD values corrected for the minimal background binding of normal human IgG or normal mouse IgG. Each value represents the average of duplicate samples and data are representative of three independent experiments.

DETAILED DESCRIPTION

In the description that follows, a number of terms used in recombinant DNA, and immunology are extensively utilized. In order to provide a clearer and consistent understanding of the specification and claims, including the scope to be given such terms, the following definitions are provided.

There are seven immunologically distinct serotypes of *Clostridium botulinum* neurotoxins, BoNT A, B, C, D, E, F, and G elaborated by various strains of *Clostridium botulinum*. They are among the most potent toxins known. Although accidental botulinum intoxication is not considered a major public health threat, clostridial neurotoxins have long been recognized as potential biowarfare or bioterrorist agents (Arnon, S. et al., 2001, JAMA 285, 1059-1070).

The term "antibody" is used in the broadest sense and includes monoclonal antibodies (including full length or intact or whole monoclonal antibodies), polyclonal antibodies, multivalent antibodies, and multispecific antibodies (e.g., bispecific antibodies).

"Antibody fragments" comprise only a portion of an intact antibody, generally including an antigen binding site of the intact antibody and thus retaining the ability to bind antigen. Example of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAB fragment (Ward et al., 1989, Nature 341, 544-546) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., 1988, Science 242, 423-426; Hudson et al., 1988, PNAS (USA) 85, 5879-5883); (x) "diabodies" with two antigen binding sites, comprising a heavy chain variable domain (VH) connected to a light chain variable domain (VL) in the same polypeptide chain (see, e.g. EP 44,097; WO93/11161; and Hollinger et al., 1993, PNAS (USA) 90, 6444-6448); (xi) "linear antibodies" comprising a pair of tandem Fd segments (VH-CH1-VH-CH1) which, together with complementary light chain polypeptides, form a pair of antigen binding regions (Zapata et al., 1995, Protein Eng. 8, 1057-1062).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, usually being directed against a single antigen, but in this application is described a monoclonal which recognizes two antigens, namely, BoNT/A and BoNT/B. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the present invention may be made by the hybridoma method first described by Kohler et al., 1975, Nature 256, 495, or may be made by recombinant DNA methods (see, e.g. U.S. Pat. No. 4,816,567). The "monoclonal antibodies" may also be isolated from phage antibody libraries using the techniques described in Clackson et al., 1991, Nature 352, 624-628; or Marks et al., 1991, J. Mol. Biol. 222, 581-597, for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al., 1984, PNAS (USA) 81, 6851-6855).

"Humanized" forms of the non-human (e.g. murine) antibodies are chimeric antibodies that contain minimal sequence derived from non-human immunoglobulin. For the most part, humanized antibodies are human immunoglobulins (recipient antibody) in which residues from a region responsible for antigen-binding, of the recipient are replaced by residues from an antigen-binding region of a non-human species (donor antibody) such as mouse, rat, rabbit, or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially the entire region corresponds to those of a non-human immunoglobulin. The humanized antibody optionally will also comprise at least a portion of an immunoglobulin constant region (Fc), typically that of a human immunoglobulin. For further details, see Presta, 1992, Curr. Op. Struct. Biol., 2, 593-596. The constant domains are not involved directly in binding an antibody to an antigen, but exhibit various effector functions, such as participation of the antibody-dependent cell-mediated cytotoxicity (ADCC).

Depending on the amino acid sequence of the constant domain of their heavy chains, intact antibodies can be assigned to different "classes". There are five major classes of intact antibodies, IgG, IgA, IgD, IgE, and IgM, and several of these may be further divided into "subclasses" (isotypes), e.g. IgG1 (including non-A and A allotypes), IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The light chains of antibodies from any vertebrate species can be assigned to one of two clearly distinct types, called kappa and lambda, based on the amino acid sequences of their constant domains.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally a CH4 domain.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

Recombinant antibodies are produced through the use of recombinant DNA technology.

In one embodiment, the present invention provides a method for producing a whole intact chimeric antibody from an antibody fragment. By chimeric is meant that the antibody is comprised of sequences or portions of antibodies derived from more than one species, e.g. the constant region is derived from a different species than the antigen binding region. The antigen-binding antibody fragment can be derived from any species, e.g. mouse, rat, rabbit, non-human primate, as long as it possesses the desired specificity. These genes could be obtained from phage display systems and phagemid vectors. Genes can also be obtained using other display technologies such as bacteria, yeast or ribosome display systems and associated vectors. Alternatively, light and heavy chain antibody genes could be obtained directly from hybridoma cell lines. PCR amplification with specific oligonucleotide primers would be required to clone and insert the genes. Examples of these systems include: lambda expression kits commercially available from Stratagene (La Jolla, Calif.) (e.g. Lambda ZAP Vector Kits) as well as phagemid vector pComb3H or pComb8 (Scripps Research Institute, La Jolla, Calif.). Genes may also be obtained from vectors used for mammalian cell expression, including, for example, commercially available vectors pCMV-Script, pDual, and pCMV-TAg1-5 vectors from Stratagene, and a variety of other systems as described by Werner et al. (1998 Drug Res. 48, 870-880) (e.g. vectors pBPV, ptPA/DHFR, pCMV/DHFR, pNEOSPLA, and pEE14). Furthermore, genes could be obtained from baculovirus expression plasmids, including, for example, pACUW51 (Pharmingen, San Diego, Calif.) or pBAC4x-1 vector systems (Novagen, Inc., Madison, Wis.).

As shown below in the Examples, the antibody fragment used in the Examples was a mouse Fab fragment obtained using phagemid display from a cDNA library of mice immunized with the pentavalent botulinum vaccine (Emmanuel et al., 2000, Biosensors & Bioelectronics 14, 751-759). The Fab fragment is specific for both BoNT/A and BoNT/B. The variable heavy chain nucleotide sequence of the BotFab5 is presented in SEQ ID NO:1. The variable light chain nucleotide sequence of the BotFab5 is presented in SEQ ID NO:2. Any desired antibody fragment having the desired antigen-binding region(s) can be used. For example, an antigen-binding region which can bind to one or more epitope derived from any of the BoNT, i.e. BoNT/A, BoNT/B, BoNT/C, BoNT/D, BoNT/E, BoNT/F, BoNT/G or any combination thereof. The antigen-binding region(s) can be specific for an epitope from an infectious agent, such as: viruses, including but not limited to dengue, rubella, Marburg, Ebola, Rift Valley fever, Lassa, Epstein-Barr, Ross River, Japanese encephalitis, Yellow fever, Human papilloma, herpes, poliovirus, and others; bacteria, including but not limited to *Burkholderia pseudomallei, Salmonella typhi, Brucella abolts, Rickettsia rickettsii, Conori australis, Yersinia pestis, Franicsella tulerensis* and others; parasites, including but not limited to *Leptosporia interrogans, Plasmodium falciparum/vivax*, and others. The antigen binding region(s) can be specific for other toxins including, but not limited to ricin, aflatoxins, T-2 mycotoxins, and enterotoxins.

In a preferred embodiment, the constant region is derived from a human antibody for use in assays on human samples. It will be appreciated, however, that the constant region may be non-human (such as bovine, canine, ovine, equine, feline, caprine, mustelid, rabbit, avian, non-human primate, or rodent) in cases where a chimeric construct is to be used as a positive antibody control in assays involving sera derived from non-human species. For assays of non-human samples from non-human subjects with BoNT intoxications, such as ducks, pheasants, chicken, mink, cattle and horses, a species specific constant region is preferred.

The constant region may consist of combinations of constant domains or epitopes thereof. The constant region may consist of two $C_H$ domains of the same type, for example, two $C_{H3}$ domains. Alternatively, the constant region may consist of two different domains from antibodies of different classes. In the Examples below, the constant region consisted of human gamma 1 and human kappa. Constant regions of different classes of antibodies may be used.

In another aspect of the invention is provided a recombinant polynucleotide molecule comprising a sequence encoding a non-human $V_H$ region, a sequence encoding a non-human $V_L$ region, and a sequence encoding a $C_H$ domain or epitope thereof.

In a preferred embodiment, the chimeric antibody is synthesized in expression vectors to generate a heavy chain expression vector and a light chain expression vector. Preferably, the $V_H$ gene is cloned next to the human Cg1 gene and the $V_L$ gene is cloned directly in front of the human Ck gene. A promoter functional in host cells is provided to control expression of the light and heavy chain. Promoters include CMV promoter, SV40 promoter, and other sequences to increase the expression of the molecule. In a preferred embodiment of the invention, the polynucleotide molecule or vector includes a sequence encoding a leader peptide which directs the synthesized polypeptide chains to the host cell periplasm. Preferably, the $V_L$ and $C_L$ and $V_H$ and $C_H$ polypeptide chains associate in the host cell periplasm and are stabilized by one or more disulphide bonds between the chains.

Examples of vectors for use in generating heavy recombinant heavy chain sequences include pHC81 (McLean et al., 2000, Mol. Immunol. 37, 837-845) or any other vectors designed for expressing heavy chain variable region. Examples of vectors for use in generating recombinant light chain include pLC (McLean et al., 2000, supra) or any other vectors designed for expressing light chain variable region. It would be clear to a person of ordinary skill in the art that certain elements of the vectors can be replaced with other elements available to a person with ordinary skill in the art without altering the essential function or purpose of the construct, for example, the antibiotic resistance marker gene, or for the purpose of adapting the vector to a different cell line or for the expression of antibodies of different species.

The recombinant vectors expressing the desired heavy chain and light chain can be introduced into host cells. Any host cell in which the construct is expressible and from which the desired antibody molecules can be isolated may be used. Host cells include but are not limited to, myeloma cells, for example YB2/0, and NSO, or Chinese hamster ovary cell lines or African green monkey COS cell lines. A variety of systems can be used in the present invention to introduce the DNA constructs described into host cells. DNA transfer may be cationic liposome-mediated, e.g. Lipofectin (Invitrogen), may be by accelerated particle delivery, by cell fusion, by electroporation, or by any other method of delivering DNA in an expressible form into a host cell. The electroporation method is detailed in the Examples below. It is understood that modifications of this protocol are within the ability of one skilled in the art.

Preferably, the transfected cells are propagated in the presence of selection pressure until only cells that have received the insert containing the drug-resistant gene and, therefore, presumably, the antibody genes, survive. After incubation, single colonies are selected to establish clonal cell lines. These cells are expanded until sufficient cell concentrations are available for analysis, usually, about 2-4 weeks. Clonal cell lines from individual colonies of cells are chosen based on the amount of antibody expressed, e.g. based on ELISA titers, and stable growth in culture. Depending upon the level of purity desired, the antibodies can be purified from cell culture supernatants using purification methods known in the art.

Any known technique for purifying the proteins of interest from the culture medium after secretion may be used, such as column affinity purification. However, because the antibody protein secreted accounts for such a high proportion of the total extracellular protein, or an amount readily detectable by ELISA of unpurified cell culture supernatant, the protein may, for certain applications, be used without further purification from other proteins. A stable IgG concentration of approximately 0.05-100 ng IgG/ml cell culture supernatant can be achieved.

The present invention further provides complete functional humanized antibodies. The chimeric humanized antibodies of the present invention have heavy and light chains associated so that the overall molecule exhibits the desired binding specificity and retains the effector functions of the molecule. As discussed previously, the antibodies described in this application are chimeric containing a variable region from a murine Fab fragment which is specific for both BoNT/A and BoNT/B, and contains a human IgG1 Fc region. This enables the antibody to be used as a positive control reagent to validate serological tests for individual exposure to BoNT/A or BoNT/B, thus obviating the need for obtaining anti-botulinum human serum for assay validation.

The antibodies of the present invention can be utilized in a method for detecting antigens specific for the antibodies in a sample suspected of containing such antigens. The method includes contacting the sample with an antibody which binds an epitope of said antigen, allowing the antibody to bind to said antigen to form an immunological complex, detecting the formation of the immunological complex and correlating the presence or absence of the immunological complex with the presence or absence of said antigen in the sample. The sample can be biological, environmental or a food sample.

The language "detecting the formation of the immunological complex" is intended to include discovery of the presence or absence of the antigen in a sample. The presence or absence of the antigen can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988 555-612). Such immunoassays include antibody capture assays, antigen direct assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a vaccine, and an antibody of the present invention, are allowed to compete for binding of the antigen. The amount of antibody bound is then measured, and a determination is made as to whether the serum contains antigen-specific antibodies. This competitive ELISA can be used to indicate immunity to known protective epitopes in a vaccine following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1-31), and Schurs, A. H. W. M., et al. 1977 (*Clin. Chim Acta* 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid such as serum, plasma, cerebral spinal fluid, urine, or blood. By "environmental sample" is meant a sample such as soil, water, and air collections. Food samples include canned goods, meats, and others.

Yet another aspect of the present invention is a kit for detecting an antigen in a biological sample. The kit includes a container holding one or more antibodies which binds an epitope of an antigen to be detected and instructions for using the antibody for the purpose of binding to said antigen to form an immunological complex and detecting the formation of the immunological complex such that the presence or absence of the immunological complex correlates with presence or absence of said antigen in the sample. Examples of containers include multi-well plates which allow simultaneous detection of a desired antigen in multiple samples.

As described in greater detail in the examples, the present inventors have isolated two recombinant monoclonal antibodies which bind to epitopes on both BoNT/A and BoNT/B. Significantly, the monoclonal antibodies are humanized and therefore useful as positive validation reagents in any of the immunoassays described above for affirming that the assay is properly detecting the desired antibody in human sera. The antibodies could be diluted in any buffer compatible within a specific diagnostic assay at a concentration dependent on assay requirement.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Materials

YB2/0 myeloma cell line was purchased from the American Type Culture Collection (Manassas, Va.), grown in RPMI-1640 with 10% FBS and maintained in standard T-75 flasks. For upscale production of antibody, cells were transferred to INTEGRA CELLine 350 bioreactor flasks (INTEGRA Biosciences, Ijamsville, Md.). Mouse anti-BoNT/A/B Fab phagemid, BotFab5 (Emanuel et al., 2000), was obtained from Dr. Peter Emmanuel (Research and Technology Directorate, U.S. Army Edgewood Chemical Biological Center, Aberdeen Proving Ground, Md.). Specialized human immunoglobulin G1 mammalian expression vectors, pLC-huCk and pHC-HuCg1 (McLean et. al. 2000), were obtained from Dr. Gary McLean (University British Coloumbia, Canada). Botulinum pentavalent toxoid (BPT) was produced by Michigan Department of Public Health (Lansing, Mich.). Undiluted, the BPT used in this work contained 9.4 ug/ml of BoNT/A and 11.8 ug/ml of BoNT/B. Normal serum immunoglobulins, conjugated and unconjugated detection antibodies were purchased from either Sigma (St. Louis, Mo.) or KPL (Gaithersburg, Md.).

Cloning of BotFab5 VH and VL

Figure 4:
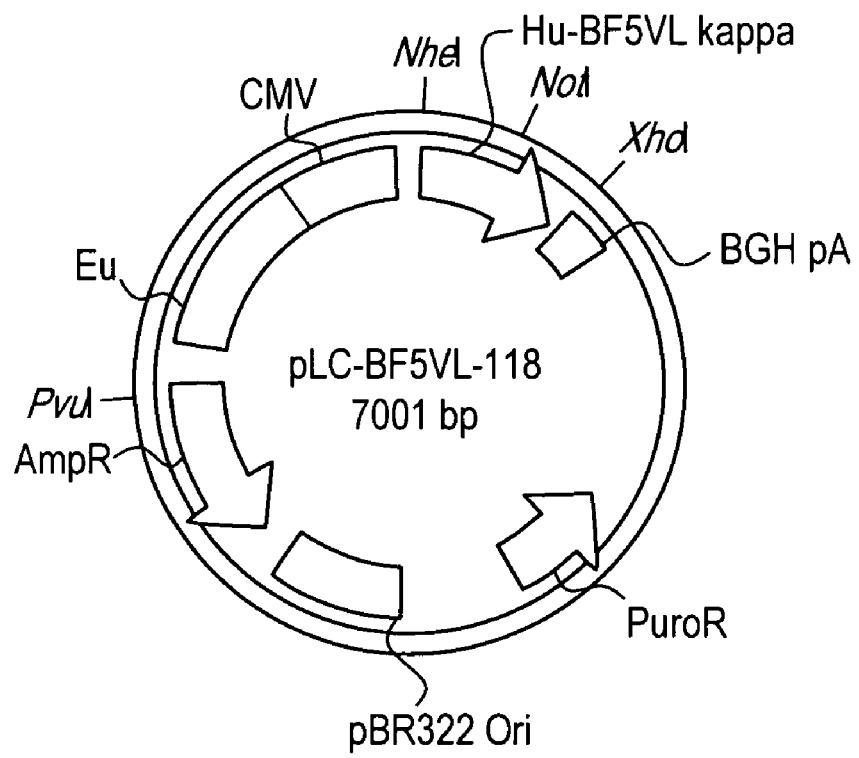
FIG. 4. Light chain expression vector, pLC-BF5VL-118. Hu-BF5VL kappa, chimeric human-BotFab5$V_L$ kappa gene; BGH pA, bovine growth hormone poly A sequence; Puro$^R$, puromycin resistance gene; pBR322 Ori, pBR322 origin sequence; AmpR, ampicillin resistance gene; Eu, murine enhancer sequence; CMV, cytomegalovirus promoter sequence.
Figure 5:
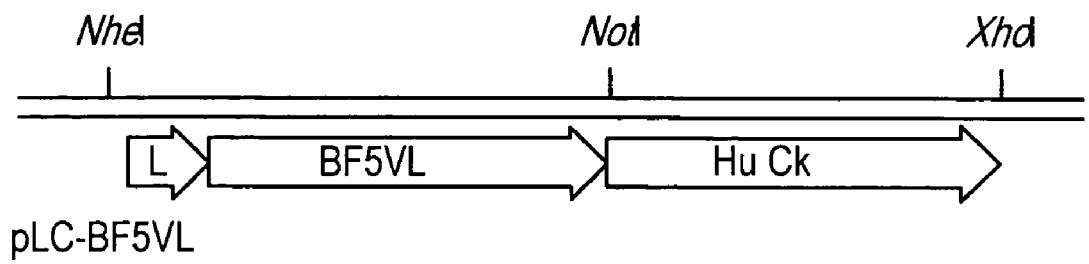
FIG. 5. Cloning site light chain expression vector, pLC-BF5VL-118. L, leader sequence; BF5VL, BotFab5 variable light chain gene (SEQ ID NO:2); Hu Ck, human kappa constant gene.

Variable heavy ($V_H$) and light ($V_L$) genes of BotFab5 were amplified by PCR using cloning primers shown in Table 1. PCR was performed using Ready-To-Go PCR Beads (Amersham Biosciences, Piscataway, N.J.) under the following thermocycler conditions: 1 cycle of 94° C. for 2 minutes, 60° C. for 2 minutes, 72° C. 2 minutes, followed by 34 cycles of 94° C. for 30 seconds, 60° C. for 30 seconds and 72° C. for 2 minutes. The $V_L$ gene was prepared for cloning into pLC-HuCk by double Nhe I and Not I restriction digestion. The $V_H$ gene was prepared for cloning into pHC-HuCg1 by double Nhe I and Hind III restriction digestion. $V_H$ and $V_L$ genes were ligated into specialized human IgG1 immunoglobulin expression vectors, pHC-Cg1 and pLC-HuCk, respectively, using Quick Ligation Kit (New England Biolabs. Ipswich, Mass.) to generate heavy chain vector, pHCBF5VH-301 (FIG. 2), and light chain vector, pLCBF5VL-118 (FIG. 4). Vector pHCBF5VH-301 contained the BotFab5 $V_H$ gene cloned directly in front of the human Cg1 gene and possessed a geneticin resistance (Neo$^R$) marker. Vector pLCBF5VL-118 contained the BotFab5 $V_L$ gene cloned directly in front of the human Cκ gene and possessed a puromycin resistance (Puro$^R$) marker. Both vectors used the CMV promoter to control expression of light and heavy chain genes.

TABLE 1

Cloning primers for the $V_H$ and $V_L$ genes of the BotFab5 phagemid.

BF5VHNHE1A
SEQ ID NO:3
5'-CTATCTATAGCTAGCTATCGAATTCGTCCTTACAATGAAATACCTAT
TGCCTACG-3'

BF5VHHIND3A
SEQ ID NO:4
5'-ATCTATCTATAAGCTTGCTGCAGAGACAGTGACCAGAGT-3'

BF5VLNHE1A
SEQ ID NO:5
5'-TCTATCTATAGCTAGCACAGCATAAACATGAAATACCTATTGCCTAC
G-3'

BF5VLNOT1A
SEQ ID NO:6
5'-TCTATCTATAGCGGCCGCAGTCCGTTTGATTTCCAGCTTGGT-3'

Transfection and Selection of Myelomas

Myeloma cells (2.0×10$^7$) were transfected with the light chain vector followed by the heavy chain vector. The vectors were linearized by Pvu I digestion and 20 μg of linearized vector was transfected into the myeloma cells by electroporation (950 μF, 0.300 kv, 1 pulse, BioRad Pulser II). Cells were first transfected with the light chain vector and grown for two weeks before selection with 5.0 μg/ml puromycin. Once a puromycin resistant population emerged, culture supernatant was clarified by centrifugation and tested by ELISA for the presence of human kappa light chain (LCκ). Puromycin resistant populations producing kappa light chain were grown to high density and electroporated with 20 μg of heavy chain vector as described above. Transfected cells were grown for three days before selection with 500 ug/ml geneticin. The resulting population of cells was maintained with 5.0 ug/ml puromycin and 500 ug/ml geneticin to yield a dually resistant population. Cells were tested by direct ELISA for the presence of whole human IgG antibody specific for the botulinum toxoid. Cells were then diluted to one cell per well to isolate clones. Twelve clones were expanded for further evaluation and two clones selected for purification by protein G HPLC.

ELISA Assays

All assays were optimized for the concentration of capture and detector antibodies individually and samples examined in duplicate on at least 3 independent assays. Human LCκ was detected in a capture ELISA using goat anti-human LCκ as the capture reagent and goat anti-human LCκ HRP conjugate as the detector reagent. ELISA plates were coated with 0.5 ug/ml of anti-human LCκ (positive capture antibody) or 0.5 ug/ml of normal goat IgG (negative capture antibody) in phosphate buffered saline (PBS) and incubated overnight at 4° C. Plates were washed three times in an automated plate washer with wash buffer (PBS, 0.1% Tween-20 and 0.01% Thimersol) before addition of sample and between all additional steps. After each step, plates were incubated at 37° C. for 1 hour (30 minutes for color development). Cell supernatants were diluted 1:2 with blocking buffer (wash buffer plus 5% dried milk) and titrated across the plate. Next detector reagent, goat-anti human LCκ HRP conjugate, was added at 0.5 ug/ml. Antibody binding was detected by the addition of ABTS® peroxidase substrate solution (KPL, Gaithersburg, Md.) and OD$_{405}$ was measured. OD$_{405}$ values were adjusted by subtracting the OD$_{405}$ value of the negative capture antibody from the OD$_{405}$ value of the positive capture antibody.

Direct and capture ELISAs were performed to characterize the recombinant antibodies and compare their performance to the parent Fab. All ELISAs used the basic technique described above. The recombinant antibodies were examined by direct ELISA to detect the presence of whole human IgG antibody specific for botulinum toxoid. Plates were coated with a 1:100 dilution of botulinum toxoid and cell supernatant, purified recombinant antibody or normal human IgG (negative control) was added at indicated concentrations and detected with 0.5 ug/ml goat anti-human IgG Fc specific HRP conjugate. As a positive control, horse anti-Bot A serum was diluted 1:100 and detected with a goat-anti horse H&L HRP conjugate. To show that each recombinant antibody retained specificity to both Bot A and Bot B, recombinant antibodies were tested in separate direct ELISA for reactivity to the individual Bot A or Bot B toxins.

The recombinant antibodies were also examined by capture ELISA to compare their performance to the parent Fab. Plates were coated with either, purified recombinant antibody, the parent BotFab5, normal human IgG (negative control for recombinant antibodies) or normal mouse IgG (negative control for Fab) at the indicated concentrations. Plates were incubated with a 1:100 dilution of the botulinum toxoid titrated 1:2 across the plate. Plates were then incubated with horse anti-botulinum A sera diluted 1:100 and detected with goat anti-horse IgG H&L HRP conjugate.

Statistics

Data are represented as the mean values ±1 SEM. Differences between two values were tested for statistical significance (P<0.05) using the two-tailed unpaired Student's t-test.

Immunoblot Analysis of Recombinant Antibodies

Proteins were separated by 8-16% SDS-PAGE electrophoresis and transferred to nitrocellulose. For detection, the blots were incubated with anti-human kappa light chain-HRP (1:1000), anti-human IgG1 Fc-HRP (1:2000) or anti-mouse (H&L)-HRP (1:5000) for one hour. Proteins were visualized with TMB peroxidase substrate.

EXAMPLE 1

Detection of Recombinant Human Anti-Botulinum IgG Antibodies

YB2/0 myeloma cells were transfected with heavy and light chain immunoglobulin plasmids (FIGS. 2 and 4, respectively) to create a recombinant human anti-botulinum toxin antibody from the variable regions of a mouse anti-botulinum Fab. The light chain expression plasmid was linearized by Pvu I digestion, transfected into YB2/0 cells by electroporation and selected by puromycin to establish a puromycin resistant population of transfectants. Human kappa light chain was detected in the supernatant of the puromycin resistant population by ELISA. Pvu I linearized heavy chain plasmid was then transfected into the kappa light chain producing, puromycin resistant population by electroporation. Selection of transfectants with both puromycin and geneticin established a dually puromycin and geneticin resistant population of cells. Supernatants from this population tested positive for the presence of human anti-botulinum IgG. Cells were diluted by RPMI-1640 supplemented with puromycin and geneticin to 1 cell per well in a 96 well culture plate to generate clonal cell lines.

Figure 6:
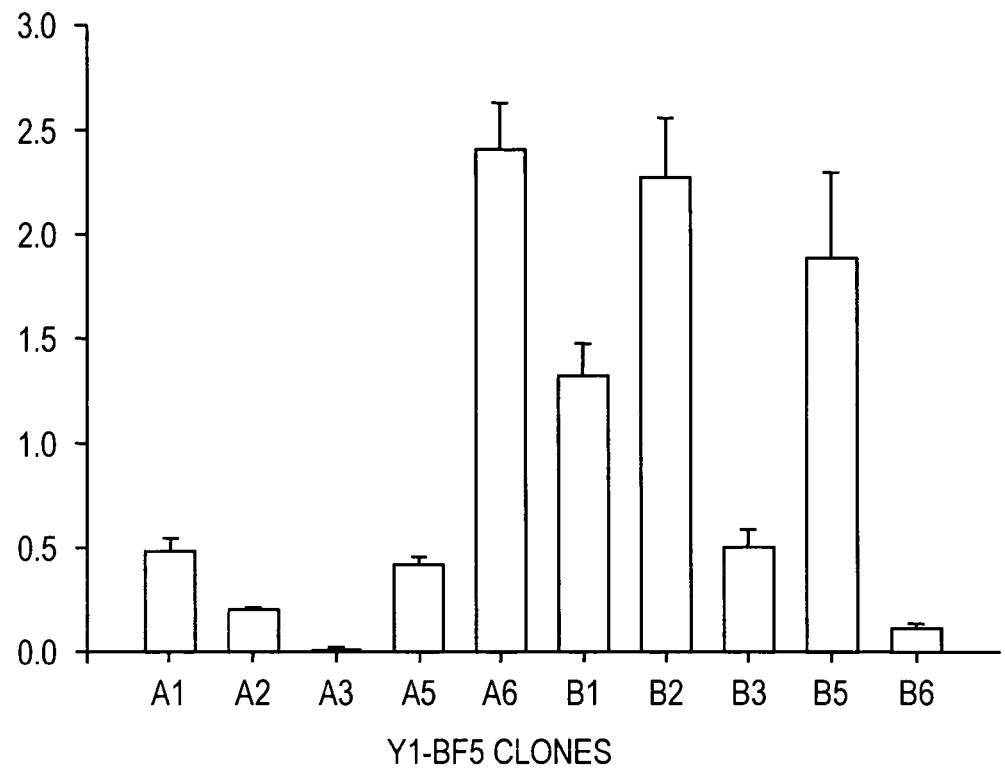
FIG. 6. Detection of rHu-BF5 in supernatants of YB2/0-BF5 clones by direct ELISA. rHu-BF5 antibodies were detected against the botulinum pentavalent toxoid (BPT).

The supernatants of twelve dually resistant clones were tested for the presence of human antibody that bound to botulinum toxoid and expressed the Fc portion of the IgG by direct ELISA. Based on corrected $OD_{405}$ readings and a conservative $OD_{405}$ cut-off point ($OD_{405} > 0.20$) seven of the clones (A1, A5, A6, B1, B2, B3, B5) produced human IgG antibody specific for botulinum toxoid (FIG. 6). Untransfected cell supernatant was also examined and showed no antibody expression above background (data not shown). From these seven clones, two clonal cell lines that had high and medium (Y1-BF5-A6 and Y1-BF5-B1 respectively) $OD_{405}$ levels were picked and expanded for characterization of the recombinant antibody.

EXAMPLE 2

Characterization of Recombinant Human Anti-Botulinum IgG Antibodies.

Recombinant clones Y1-BF5-A6 and Y1-BF5-B1 were transferred for growth in INTEGRA bioreactor flasks. Supernatant was collected over 4 weeks and purified by G-protein HPLC. The antibody fraction from the protein G column was collected, concentrated and protein concentrations determined. The purified antibodies, rHu-BF5-A6 and rHu-BF5-B1, were examined for binding to the botulinum toxoid by direct and capture ELISA.

Figure 7:
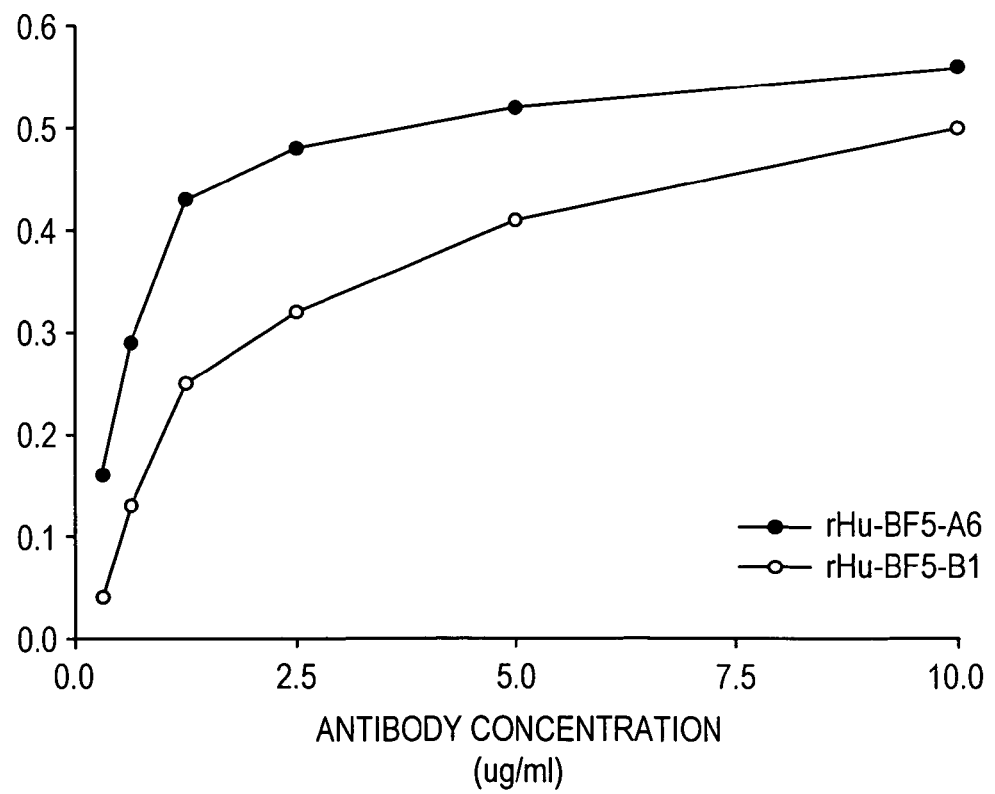
FIG. 7. Direct ELISA binding affinity curves of rHu-BF5 reactivity to botulinum pentavalent toxin (BPT). For direct ELISA, plates were coated with 1:100 dilution of botulinum toxoid and incubated with indicated amounts of the purified A6 or B1 antibodies. Antibodies were detected with 0.5 ug/ml goat anti-human IgG Fc HPR conjugated antibody.

In the direct ELISA, the purified recombinant antibodies demonstrated binding to a 1:100 dilution of botulinum toxoid over a range of antibody concentrations from 10 ug/ml to 1.25 ug/ml (FIG. 7). Using the lowest antibody concentration, this correlates to a detection limit of 9.4 ng botulinum toxoid A and 11.8 ng botulinum toxoid B in our direct ELISA assay. Direct ELISA of recombinant antibodies against individual Bot A or Bot B toxins indicated that the antibodies retain specificity to both Bot A and Bot B toxins.

Figure 8:
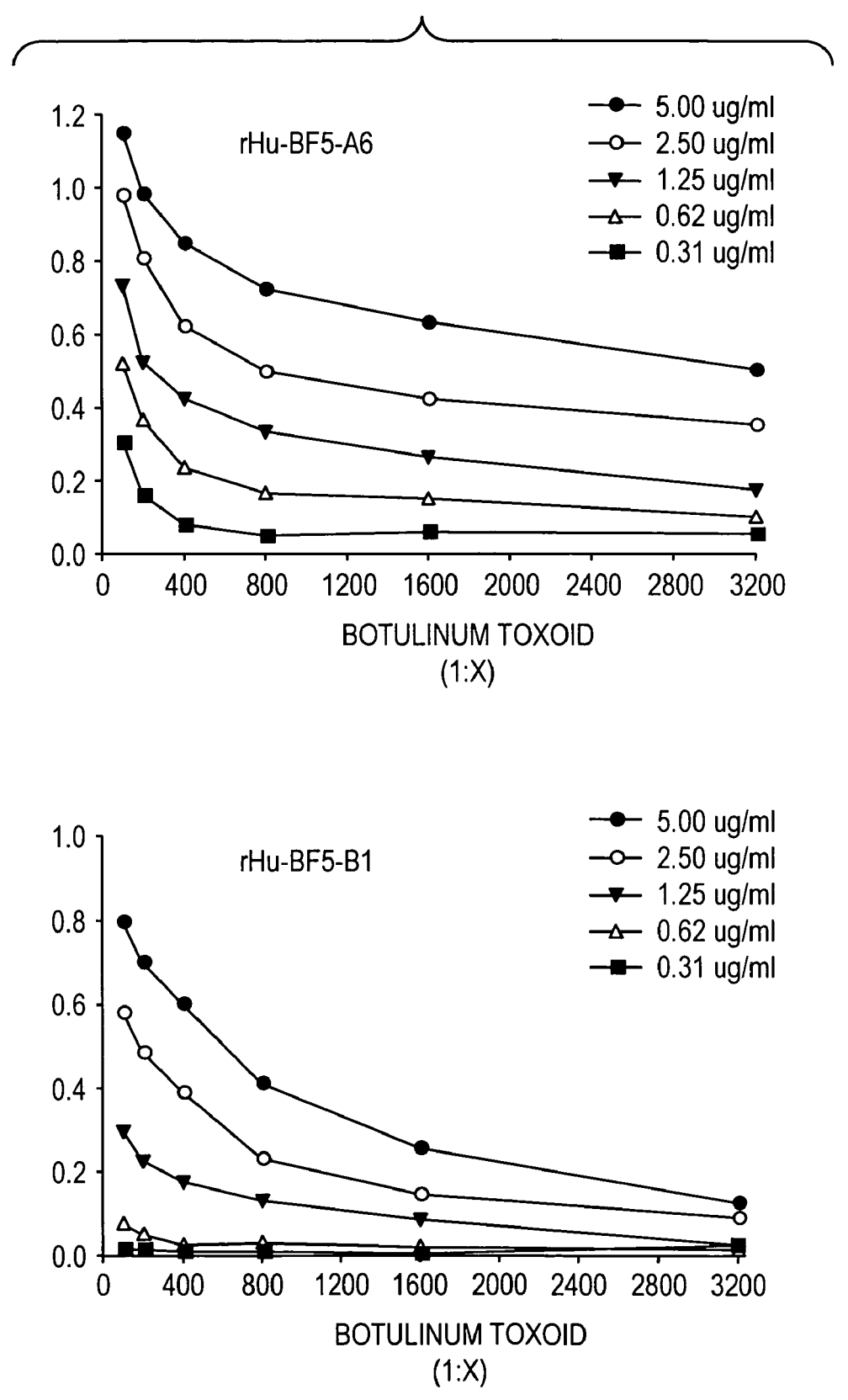

In the capture ELISA, either recombinant antibody demonstrated binding to the botulinum toxoid over a range of toxoid dilutions from 1:100 to 1:3200 (FIG. 8) when the antibody concentration was constant at 5.0 ug/ml. This correlates to a detection limit of 0.29 ng Botulinum toxoid A and 0.35 ng Botulinum toxoid B in our capture ELISA assay.

Figure 9:
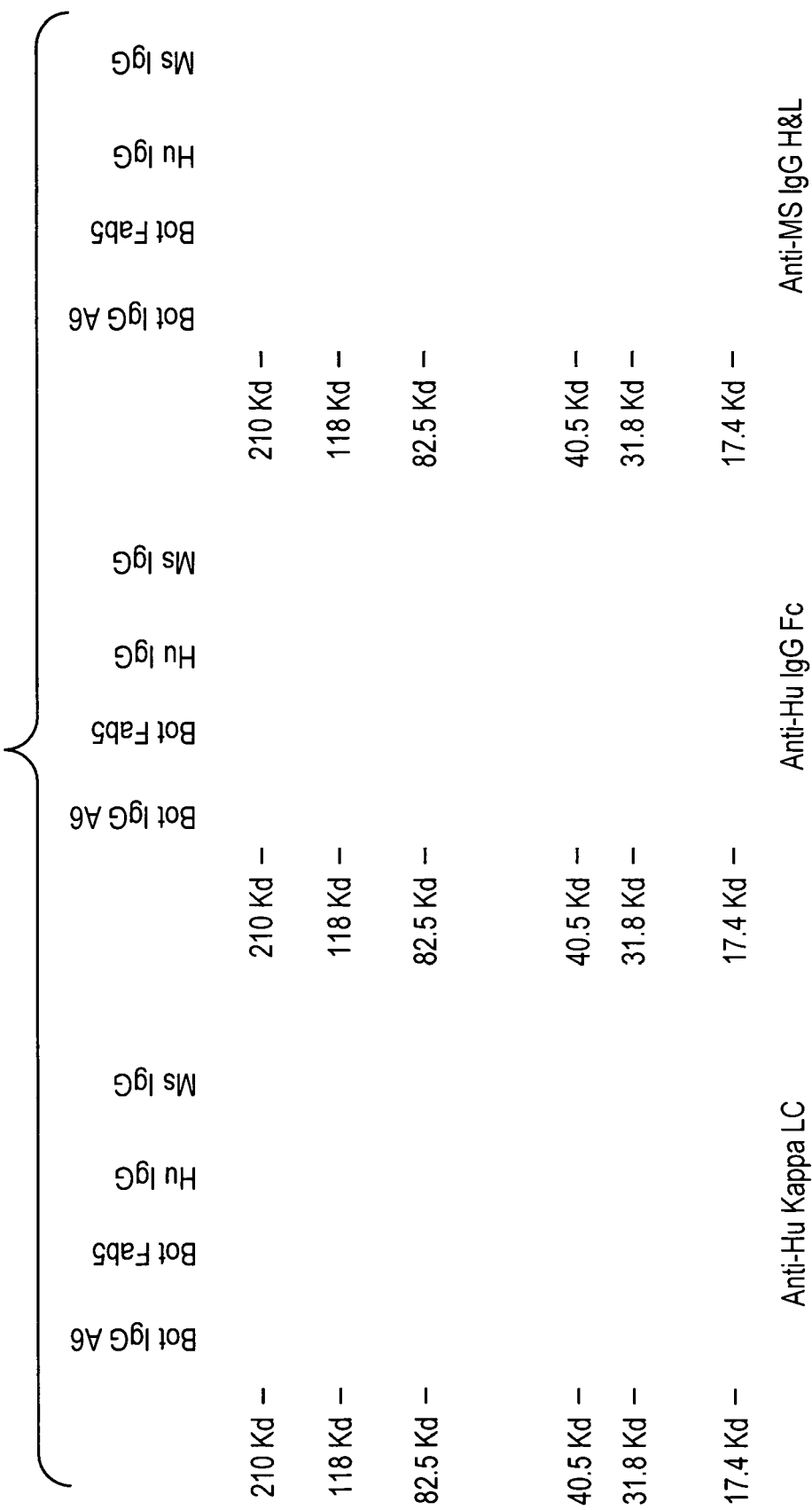
FIG. 9. Immunoblot analysis of purified rHu-BF5 antibodies. Purified recombinant antibody A6 (2 ug), BotFab5 (2 ug), normal human IgG (1 ug) or normal mouse IgG (1 ug) were separated by SDS-PAGE under reducing conditions. Blots were detected with either anti-human kappa light chain, anti-human IgG Fc or anti-mouse IgG H&L. Molecular weight markers are shown on the left of each blot. Blots are representative of three independent experiments.

To further confirm that the myeloma cells expressed recombinant, whole human IgG antibody, purified antibodies were examined by immunoblot analysis. Purified recombinant antibody rHu-BF5-A6, BotFab5, normal human IgG and normal mouse IgG were separated by SDS-PAGE. Proteins were detected with anti-human kappa light chain-HRP, anti-human IgG Fc-HRP or anti-mouse IgG (H&L)-HRP. Incubation of the nitrocellulose with anti-human kappa light chain HRP conjugate revealed a light chain band in the recombinant A6 antibody but not the BotFab5 compared to the human IgG positive control (FIG. 9). Likewise, incubation with anti-human IgG Fc specific HRP conjugate demonstrated the presence of the Fc portion of the heavy chain in the recombinant A6 but not the BotFab5. Further, incubation with an anti-mouse HRP conjugate demonstrated zero bands present in the recombinant A6 antibody, but a single band around the size of the mouse light chain in the BotFab5, supporting the full conversion from a mouse Fab to a human IgG.

EXAMPLE 3

Comparison of Recombinant Human IgG Antibodies to Mouse BotFab5

Figure 10:
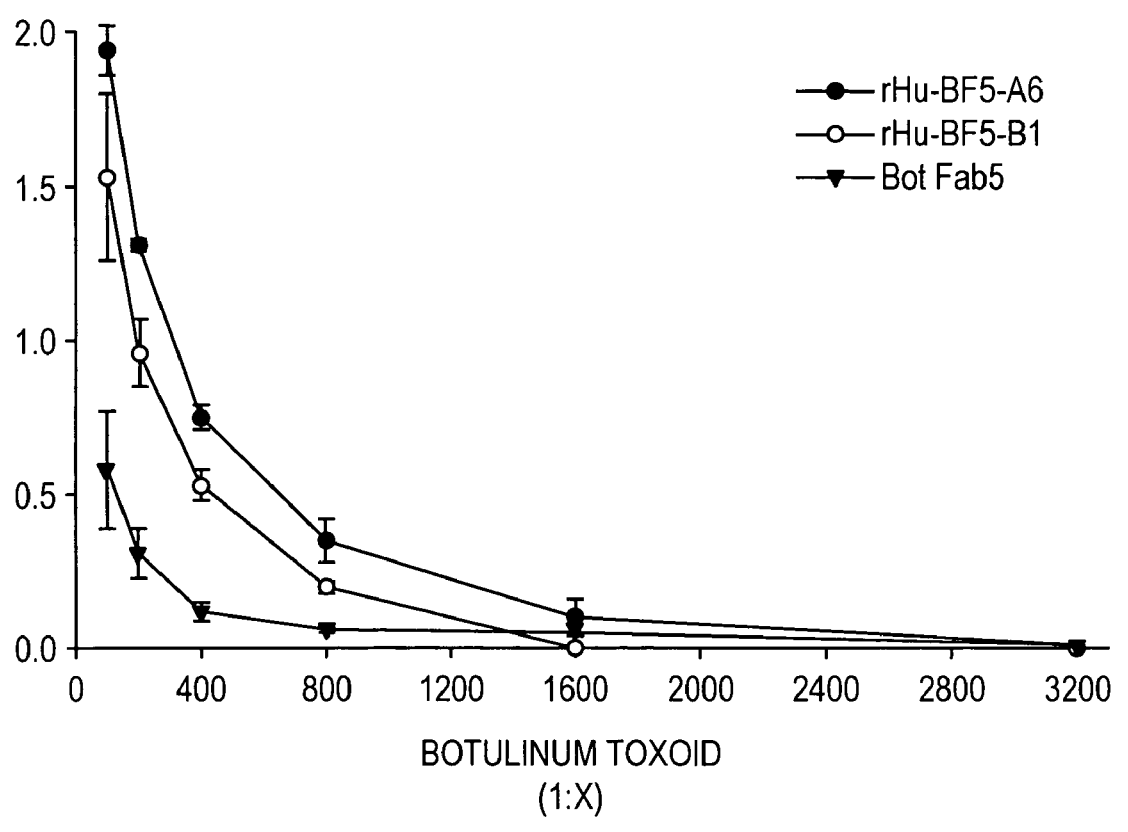

The purpose of these studies was to create a recombinant human IgG antibody that could perform equal to or better than the parent Fab. Therefore, after verifying that the myeloma cells were indeed producing whole human IgG antibodies against botulinum toxoid, it was important to compare the recombinant antibodies to the parent Fab in our diagnostic assays. Comparing the recombinant antibodies to the Fab in a direct ELISA is not feasible because the two reagents would require separate conjugated antibodies for detection. Therefore the recombinant antibodies and the Fab were examined for binding ability to Botulinum toxoid in a capture ELISA. By this means, the plates are exposed to the exact same antigen and conjugated antibodies. Both rHu-BF5-A6 and rHu-BF5-B1 performed better than the BotFab5 at capture concentrations of 2 ug/ml (FIG. 10) and 0.5 ug/ml.

Discussion

BotFab5 is an anti-botulinum toxin Fab that was selected from a phage display library prepared from mice immunized with the botulinum pentavalent toxoid. BotFab5 possesses high affinity and cross-reactivity to both botulinum toxin A and toxin B. Although useful for the immunodetection of botulinum toxin, as a murine Fab, BotFab5 has several drawbacks when compared with whole IgG antibodies. First, while useable in immunoassays, Fab molecules are less compatible with rapid and field formats such as ELISA and ECL which favor whole IgG antibody as reagents. Second, Fab are less efficient to purify and label than whole IgG. Third, as a murine Fab, BotFab5 can not be used as a positive control during human serological analysis for exposure to botulinum toxin.

To improve the utility of BotFab5 for the immunodetection and serological assay of botulinum toxin exposure, BotFab5 was reformatted as a chimeric human IgG antibody. The BotFab5 Fab VL and $V_H$ genes were cloned into specialized human IgG1 expression vectors, pLC-huck and pHC-cg1, respectively. Vectors were linearized and transfected into myeloma cells by electroporation. Recombinant chimeric human anti-botulinum IgG antibody was expressed, secreted into and detected in transfected myeloma culture supernatants. Two clonal myeloma cell lines, Y1-BF5-A6 and Y1-BF5-B1, were isolated and recombinant chimeric human anti-botulinum IgG monoclonal antibodies, rHu-BF5-A6 and rHu-BF5-B1, were purified from the culture supernatants.

Western blot analysis was used to confirm human IgG was expressed by the transfected myeloma cell lines. Western blot of the rHu-BF5-A6 antibody and its parent BotFab5 Fab showed that human kappa light chain and human IgG Fc were present in the rHu-BF5-A6 antibody, but not in the parent BotFab5 Fab, while mouse antibody proteins were detected only in the BotFab5 Fab.

rHu-BF5-A6 and rHu-BF5-B1 were characterized by direct and capture ELISA, using the botulinum toxoid as the test antigen. Direct ELISA demonstrated that as low as 1.25 ug of either rHu-BF5-A6 and rHu-BF5-B1 detected a 1:100 dilution of botulinum toxoid. Direct ELISA of rHu-BF5-A6 and rHu-BF5-B1 for reactivity to individual Bot A and Bot B toxins showed no loss of specificity or cross-reactivity to either Bot A or Bot B. In capture ELISA, 2.0 ug of either rHu-BF5-A6 and rHu-BF5-B1 detected as low as a 1:800 dilution of botulinum toxoid, a 4-fold improvement over the parental BotFab5 Fab.

Reformat of the BotFab5 Fab anti-botulinum binding domains as a chimeric human IgG incurred no detectable loss of affinity or specificity upon rHu-BF5-A6 or rHu-BF5-B1 for the botulinum toxoid. Rather, the ability to detect the botulinum toxoid improved when converted into the human IgG format.

The ability to convert antibody fragments into whole human antibodies dramatically improves their utility for biodefense applications. This is because the whole IgG format overcomes several shortcomings associated with using of antibody fragments as immunoassay reagents, especially in field environments and for serological analysis of exposure to biological threat agents. Coupled with the increasing sophistication of antibody display and engineering technologies, isotype conversion, especially into the human IgG format, will increasingly generate a wide variety of high quality antibody reagents for the detection and serological analysis of biological agents.

What is claimed is:

1. The antibody rHu-BF5-A6 produced by the myeloma cell line Y1-BF5-A6, having ATCC accession no. PTA-7673.

2. A composition comprising the antibody of claim 1.

3. The antibody of claim 1, wherein said antibody is labeled with a label chosen from the group consisting of a radioactive label, an enzyme label, and a fluorochrome.

4. The antibody rHu-BF5-B1 produced by the myeloma cell line Y1-BF5-B1, having ATCC accession no. PTA-7674.

5. A composition comprising the antibody of claim 4.

6. The antibody of claim 4, wherein said antibody is labeled with a label chosen from the group consisting of a radioactive label, an enzyme label, and a fluorochrome.

7. A method for detecting, in a sample, one or more botulinum neurotoxin chosen from the group consisting of BoNT/A and BoNT/B, said method comprising:

(i) incubating the sample with an effective amount of at least one antibody chosen from the group consisting of rHu-BF5-A6 produced by the myeloma cell line Y1-BF5-A6, having ATCC accession no. PTA-7673 and rHu-BF5-B1 produced by the myeloma cell line Y1-BF5-B1, having ATCC accession no. PTA-7674, under conditions which allow the formation of an antibody-antigen complex; and (ii) detecting the antibody-antigen complex wherein the presence or absence of the complex indicates the presence or absence of said botulinum neurotoxin in said sample.

8. The method of claim 7, wherein said sample is chosen from the group consisting of a biological sample, an environmental sample and a food sample.

9. A kit for detecting one or more botulinum neurotoxin, said botulinum neurotoxin chosen from the group consisting of BoNT/A or BoNT/B, in a biological sample, said kit comprising:

(1) a container holding at least one monoclonal antibody chosen from the group consisting of rHu-BF5-A6 produced by the myeloma cell line Y1-BF5-A6, having ATCC accession no. PTA-7673 and rHu-BF5-B1 produced by the myeloma cell line Y1-BF5-B1, having ATCC accession no. PTA-7674, and (2) instructions for using said antibody for the purpose of binding to one or more of said neurotoxin to form an immunological complex and detecting the formation of the immunological complex such that presence or absence of immunological complex correlates with presence or absence of said neurotoxin in said sample.

10. The continuous myeloma cell line Y1-BF5-A6 having deposit accession number PTA-7673, and clones thereof.

11. The continuous myeloma cell line Y1-BF5-B1 having deposit accession number PTA-7674, and clones thereof.

12. A method for capturing one or more botulinum neurotoxin chosen from the group consisting of BoNT/A and BoNT/B from a sample, said method comprising contacting said sample with a monoclonal antibody specific for both BoNT/A and BoNT/B chosen from the group consisting of rHu-BF5-A6 produced by the myeloma cell line Y1-BF5-A6 having ATCC accession no. PTA-7673 and rHu-BF5-B1 produced by the myeloma cell line Y1-BF5-B1, having ATCC accession no. PTA-7674, and isolating the complex formed between the neurotoxin in the sample and the monoclonal antibody.

13. The method of claim 12 wherein said sample is selected from the group consisting of biological sample, an environmental sample and a food product.

* * * * *

SEQUENCE LISTING

<160> NUMBER OF SEQ ID NOS: 6

<210> SEQ ID NO 1
<211> LENGTH: 351
<212> TYPE: DNA
<213> ORGANISM: Mus musculus
<220> FEATURE:

<400> SEQUENCE: 1

```
gaggttcagc ttcagcagtc tggggcagag cttgtgaagc                    40 cagggcctc agtcaagttg tcctgcacag cttctggctt                     80
caacattaaa gacacctta tgcactgggt gaagcagagg                    120
cctgaacagg gcctggagtg gattggaagg attgatcctg                   160
cgaatgggaa tactgaatat gacccgaagt tccagggcaa                   200
ggccactata acagcagaca catcctccaa cacagtcaac                   240
ctgcagctca gcagcctgac atctgaggac actgccgtct                   280
attactgtgc tagtggaggg gaactggggt ttccttactg                   320
gggccaaggg actctggtca ctgtctctgc a                            351
```

<210> SEQ ID NO 2
<211> LENGTH: 303
<212> TYPE: DNA
<213> ORGANISM: Mus musculus
<220> FEATURE:

<400> SEQUENCE: 2

```
gacatccaga tgacccagtc tccagcctcc ctatctgcat                    40
ctgtgggaga aactgtcact atcacatgtc gagcaagtgg                    80
gaatattcac aattatttag catggtatca gcagaaacag                   120
ggaaaatctc ctcagctcct ggtctataat gcaaaaacct                   160
tagcagatgg tgtgccatca aggttcagtg gcagtggatc                   200
aggaacacaa tattctctca agatcaacag cctgcagcct                   240 gaagatttg ggagttatta ctgtcaacat ttttggagta                    280
ctccgtggac gttcggtgga ggc                                     303
```

```
<210> SEQ ID NO 3
<211> LENGTH: 55
<212> TYPE: DNA
<213> ORGANISM: Artificial Sequence
<220> FEATURE:
<223> OTHER INFORMATION: primer

<400> SEQUENCE: 3
ctatctatag ctagctatcg aattcgtcct tacaatgaaa                                  40
tacctattgc ctacg                                                             55

<210> SEQ ID NO 4
<211> LENGTH: 39
<212> TYPE: DNA
<213> ORGANISM: Artificial Sequence
<220> FEATURE:
<223> OTHER INFORMATION: primer

<400> SEQUENCE: 4
atctatctat aagcttgctg cagagacagt gaccagagt                                   39

<210> SEQ ID NO 5
<211> LENGTH: 48
<212> TYPE: DNA
<213> ORGANISM: Artificial Sequence
<220> FEATURE:
<223> OTHER INFORMATION: primer

<400> SEQUENCE: 5
tctatctata gctagcacag cataaacatg aaatacctat                                  40
tgcctacg                                                                     48

<210> SEQ ID NO 6
<211> LENGTH: 42
<212> TYPE: DNA
<213> ORGANISM: Artificial Sequence
<220> FEATURE:
<223> OTHER INFORMATION: primer

<400> SEQUENCE: 6
tctatctata gcggccgcag tccgtttgat ttccagcttg                                  40
gt                                                                           42
```